(12) United States Patent
Schwartz et al.

(10) Patent No.: US 11,680,902 B2
(45) Date of Patent: Jun. 20, 2023

(54) METHOD OF INTRINSIC SPECTRAL ANALYSIS AND APPLICATIONS THEREOF

(71) Applicant: Center for Quantitative Cytometry, San Juan, PR (US)

(72) Inventors: Abraham Schwartz, San Juan, PR (US); Frank Mandy, Ontario (CA)

(73) Assignee: Center for Quantitative Cytometry, San Juan, PR (US)

( * ) Notice: Subject to any disclaimer, the term of this patent is extended or adjusted under 35 U.S.C. 154(b) by 8 days.

(21) Appl. No.: 17/067,952

(22) Filed: Oct. 12, 2020

(65) Prior Publication Data

US 2022/0113253 A1 Apr. 14, 2022

(51) Int. Cl.
 *G01N 21/64* (2006.01)
 *G16C 20/64* (2019.01)

(52) U.S. Cl.
 CPC ......... *G01N 21/6428* (2013.01); *G16C 20/64* (2019.02); *G01N 2021/6439* (2013.01)

(58) Field of Classification Search
 CPC ....... G01N 21/6428; G01N 2021/6439; G16C 20/64
 See application file for complete search history.

(56) References Cited

U.S. PATENT DOCUMENTS 10,337,916 B1 * 7/2019 Schwartz ................. G01J 3/28
10,670,512 B1 * 6/2020 Schwartz ........... G01N 15/1429

FOREIGN PATENT DOCUMENTS

KR 102175194 * 11/2020 ............ G01J 3/2889

OTHER PUBLICATIONS

Siddiqui et al. (Cancer (Cancer Cytopathology) vol. 114, No. 1, pp. 13-21, 2008 (Year: 2008).*

* cited by examiner

*Primary Examiner* — David P Porta
*Assistant Examiner* — Meenakshi S Sahu
(74) *Attorney, Agent, or Firm* — Hoglund & Pamias, PSC; Roberto J. Rios

(57) ABSTRACT

A library of known intrinsic spectra is provided to identify at least one known material in a sample of interest. The library includes individual intrinsic spectra channels defined by the assignment of intrinsic spectra of at least one known material, and combinations thereof, so that the assigned intrinsic spectra of each intrinsic spectra channel is correlated to at least one known material. The at least one known material is identified in the sample of interest when intrinsic spectra obtained from the sample of interest is matched to an assigned intrinsic spectra of an intrinsic spectra channel of the library of known intrinsic spectra.

7 Claims, 7 Drawing Sheets

Intrinsic Flow Cytometer Analysis Report
(Simulation)

| CD Marker | Percent Cell Population | Fluorescent Labels |
|---|---|---|
| CD 3 | 32 | FITC |
| CD4 | 43 | PE |
| CD8 | 14 | Percp-Cy5.5 |
| CD3/CD4 | 21 | FITC/PE |
| CD3/CD8 | 12 | FITC/Percp-Cy5.5 |
| CD4/CD8 | 33 | PE/Percp-Cy5.5 |
| CD3/CD4/CD8 | 32 | FITC/PE/Percp-Cy5.5 |
| Un-Labeled | 11 | None |

Total Cell Count 10,386

Intensity Histograms (a) Original Focused Image (b) Diffused/Unfocused Image (c) Original Image after intrinsic processing b) Intrinsic Image   c) Simulated Image of   d) Simulated Image of
                        Isolated Chlorophyll b   Enhanced Chlorophyll b

METHOD OF INTRINSIC SPECTRAL ANALYSIS AND APPLICATIONS THEREOF

TECHNICAL FIELD

The invention relates to the analysis of spectral data generated from intrinsic instruments. Specifically, this invention is directed to the identification and presentation of known materials from the spectral data. More specifically, this invention is directed to the identification and presentation of known materials by analysis spectral data obtained by intrinsic flow cytometers and intrinsic imaging instruments.

BACKGROUND OF THE INVENTION

Spectra generated by dynamic flow instruments, such as an intrinsic flow cytometer, and imaging instruments that produce intrinsic multi-spectral and hyper-spectral images can be highly complex. This is because the intrinsic spectra can contain a mixture of intrinsic spectra unique to each separate material, with each intrinsic spectrum containing intrinsic absorption, emission, and intrinsic spectra reflection components. The ability to identify specific materials from these raw instrument intrinsic spectra depends on being able to isolate the specific intrinsic spectra representing each material, respectively.

For flow cytometers, it is necessary to analyze and isolate the intrinsic spectra from each labeled cell passing through the fluorescence detection system of the instrument and to de-convolute multiple fluorescent labels that may be labeling specific cell populations.

In the case of digital imaging instruments where each pixel of an image carries with it an intrinsic spectrum, the problem becomes more difficult because of the mega number of pixels and the possible mixed intrinsic spectra associated with each pixel.

The spectral signal detection system of most flow cytometers is based on a design of fixed fluorescence channels as they are defined by narrow band pass filters and dichroic mirrors to detect a portion of the emission spectra from fluorochromes tagged to monoclonal antibodies (MAbs). Such detection systems utilize only a small range of the emission spectra from the fluorochromes. In conventional flow cytometry, difficulties arise because of spectral spillover with multiple fluorochromes as they are collected into a single channel directed by band pass filters. In such situation the emission spectra wavelength range of most fluorochromes are broad compared to the band pass filters. The spectral overlap can contribute to errors in population detection. In general, the problem has been addressed with mathematical color compensation. An example is where the degree of overlap is estimated and corrected for two populations and displayed on an orthogonal two-dimensional (2D) dot plots. This spectral overlap problem is frequent. In clinical flow cytometry, it occurs even with some of the most commonly used paired fluorochromes, i.e., fluorescein and phycoerythrin. The continuous discovery of new receptors and roles these cellular epitopes perform inside and on the surface of cells requires a more flexible strategy to monitor poly-chromatic fluorochrome labels, including managing wider wavelength ranges. To address the above demand, the number of detection channels and excitation lasers have increased to broaden the detection and illumination range from UV to near IR. Currently, 12 to 15 fluorescence channels have been generated for a single flow cytometer assay. The fluorescence epitope data analysis from such assays are extremely complex and can be confusing, especially when trying to present the cell population data, where only software generated color compensation is available.

Accordingly, what is needed is a system and a methodology that solves the above-explained technical problems by identifying and presenting cell population data without the spectral overlap that contributes to errors in population detection and by reducing the need of generating a large number of difficult to visualize 3D and higher dimensionality dot plots, all without the use of error prone subjective gates.

SUMMARY OF THE INVENTION

The concept of fluorescence channels for instruments such as the epi-fluorescence microscope and the flow cytometer is derived from the physical act of limiting the wavelength ranges of the illumination and resulting emissions by dichroic mirrors and band pass filters. After the illumination impinges on the sample, the illumination that is now considered irrelevant, is directed away from the emission detectors, e.g., the photomultiplier tubes, cameras or the human eye by an optical path comprised of short pass filters dichroic mirrors. The remaining spectral component, the emission, is directed through narrow band pass filters to the detectors. These paths are considered the fluorescence channels of the instruments.

However, with instruments that are based on intrinsic technology, the illumination wavelength range that is not absorbed by the sample is eliminated, along with foreground and background spectral components, by direct subtraction leaving only the intrinsic spectrum of the sample, i.e., the intrinsic absorption and emission spectral components. In the case of the present invention, these intrinsic spectra are considered the fluorescence channels of the intrinsic instrument.

The present invention defines the fluorescence channels and the sample analysis necessary to identify specific materials from raw instrument intrinsic spectra by isolating the specific intrinsic spectra representing each material, respectively.

The spectral detection system of an Intrinsic Hyper-Spectral Flow Cytometer does not require narrow band filters or dichroic mirrors. For illumination, it uses an unfiltered broad wavelength range illumination source. The fluorescence channels are defined by the intrinsic spectra of the fluorochrome labels used in the assay. The intrinsic spectrum of a fluorochrome is complex since it contains both intrinsic absorption and emission spectral components. The intrinsic spectra become more complex when analyzing a mixture of cells in a specimen. Some cells may have several different epitopes/receptors attach to antibodies with corresponding fluorochromes. In this case, the intrinsic spectrum of a cell will contain the sum of all the intrinsic spectral components of all bound fluorescent labels.

To separate and identify a cell population, the intrinsic spectrum from each cell is matched to confirm its profile against a library of known intrinsic spectra that represent the known fluoro chromes in the assay. These fluorescence channels can be displayed in a 2D dot plots format, as it is presented with traditional compensated flow cytometry data. The intrinsic spectrum contained in the library of each known fluorochrome and combination(s) thereof, is generated by de-convolution of the sum of the known intrinsic spectra of the fluorochromes in the assay. This match is achieved because the known intrinsic spectra defining the fluorescence channels are constructed exclusively from intrinsic absorption and emission spectral components of each fluorochrome used to label the antibodies for analysis. The use of intrinsic spectra to define fluorescence channels simplifies cell identification and helps eliminate counting errors. Subjective color compensation has been found to induce some errors in traditional multicolor flow cytometry. With the intrinsic spectral analysis of the present invention, there is no compensation required for spectra overlap, and there is no interference generated by narrow band pass filters.

The intrinsic spectral analysis and methodology of the present invention improves the current flow cytometry technology by eliminating all the interference generated by dichroic mirrors and narrow band pass filters and any compensation needed for spectra overlap among channels. This improvement is primarily achieved by the generation and implementation of a library of known intrinsic spectra, which is associated to at least one known fluorochrome of interest, that replaces dichroic mirrors, narrow band pass filters and mathematical color compensation used in conventional flow cytometry.

In conventional flow cytometry, dichroic mirrors and narrow band pass filters are used to detect a small range or portion of the whole emission spectra from the fluorochromes on each cell. In contrast, the present invention uses the library of known intrinsic spectra in conjunction with the whole intrinsic spectra of a cell to detect, identify and quantify the presence of at least one known labelling fluorochrome on each cell.

In addition, the intrinsic spectral analysis and methodology of the present invention improves the current intrinsic imaging technology. Intrinsic imaging instruments produce intrinsic spectra associated with each pixel of a field of view where many of the contributing intrinsic spectra may be unknown, so complete identification of the materials in an image may not be accurate or feasible at all. The identification is done by using just a peak of the raw spectra that may identify a known material of interest.

However, the present invention uses the library of known intrinsic spectra and its associated methodology to positively identify or proof the absence of a known material of interest in an intrinsic image by matching the whole intrinsic spectrum of the known material to the whole intrinsic spectrum of the pixels of the image. Thus, intrinsic spectra taken individually, and all their combinations is used to determine the spatial location and associations of these known materials in the image by pixel spectral matching.

Moreover, the system and method of the present invention also avoids occurrence of Raman shifts, which often occurs when using narrow band illumination. An additional advantage of this de-convolution method is that each fluorescence channel defines a spectrally finite cell population. In this way, data can be reported in a list of single or multiple fluorochrome defined channels, replacing the traditional 2-dimensional dot plots.

Clinical utilization of fluorochromes for immunophenotyping is expanding on two fronts, the demand for both the number of epitopes per cell and for the number of different phenotypes present in a specimen are increasing. Intrinsic spectral flow cytometry can support such advanced demand because of the limitless possibilities for combination of markers with the de-convolution driven analysis to define both normal and abnormal immunophenotypes.

BRIEF DESCRIPTION OF THE DRAWINGS

Further features and advantages of the invention will become apparent from the following detailed description taken in conjunction with the accompanying figures showing illustrative embodiments of the invention, in which.

Figure 1A:
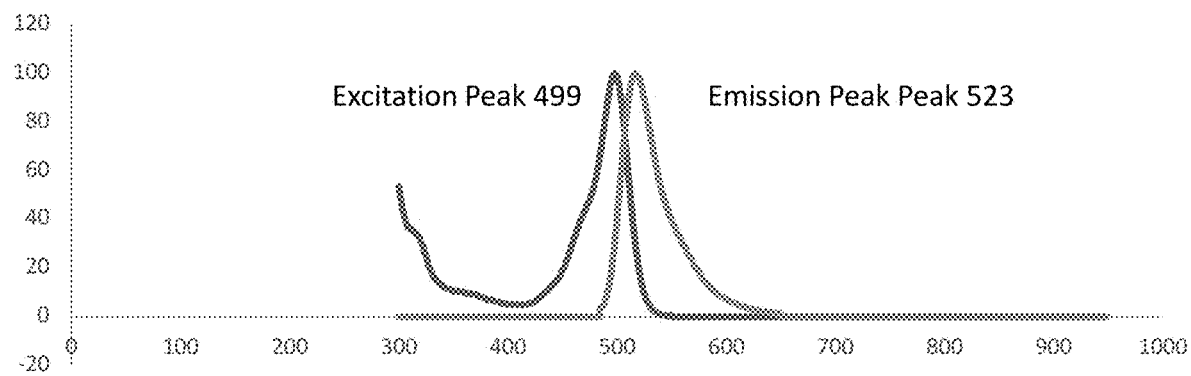
FIG. 1a illustrates fluorescence spectral components of fluorescein isothiocyanate (FITC) and how they relate to intrinsic spectra showing excitation and emission components obtained from a spectrofluorometer.

Throughout the figures, the same reference numbers and characters, unless otherwise stated, are used to denote like elements, components, portions or features of the illustrated embodiments. The subject invention will be described in detail in conjunction with the accompanying figures, in view of the illustrative embodiments.

DETAILED DESCRIPTION OF THE INVENTION

Recently, a new Intrinsic Hyper-Spectral Flow Cytometer has been proposed that does not use narrow band filters and dichroic mirrors to define its fluorescence channels. Rather, this new instrument generates intrinsic spectra of the individual cells, as described in U.S. Pat. No. 10,670,512 B1, incorporated herein by reference in its entirety. The analysis of intrinsic spectra obtained from a cell sample labeled with multiple fluorochromes starts with a physical de-convolution of the cell spectra where the irrelevant illumination, i.e., the illumination not absorbed by the cell, is eliminated, revealing the intrinsic spectrum of the cell. These intrinsic spectra contain the intrinsic absorption and emission components of each of the fluorochromes. This process is described in the U.S. Pat. Nos. 9,435,687, 10,670,512, and U.S. application Ser. No. 16/888,660, incorporated herein by reference in their entirety.

Briefly explained, an instrument is calibrated. Each analyte passing through the excitation beam is correlated with its focused and defocused/diffused spectral data and processed by subtracting the defocused/diffused spectrum from the focused spectrum. The resulting spectra are averaged pixel by pixel across the wavelength range of the excitation energy to yield the Average Residual Spectrum (ARS) at the specific instrument settings. The ARS is then added back into each of the defocused/diffused spectra and the adjusted defocused/diffused set of spectra are subtracted from the focused spectra of each analyte, respectively. This process produces a Zero Order Spectrum (ZOS) for the analyte that has a zero value across its entire excitation wavelength range validating that the instrument is calibrated and ready to collect intrinsic spectral data. Without changing the instrument settings, the analyte of interest is run and the ARS from the calibration step is added to the spectra of each analyte of the defocused/diffused data stream. These adjusted defocused/diffused spectra are then subtracted from the corresponding focused spectra of each analyte. This procedure generates the intrinsic spectra of the analytes that contains both the absorption and fluorescence spectral components across the excitation wavelength range.

Thus, the elimination of the irrelevant illumination is accomplished by either subtracting the defocused or the translucent/diffused spectrum from the illumination focused on the fluidic stream. Accordingly, the present invention validates and applies the de-convolution methodology that defines the fluorescence channels to which the intrinsic spectrum of each cell is matched.

Construction of an Intrinsic Fluorescence Channel Library

In general, the analysis of intrinsic spectra is based on comparison of the intrinsic spectra of a sample of interest to an intrinsic spectrum in a library of known spectra that are obtained directly from intrinsic spectrometry instrumentation from the known material of interest, as explained in U.S. Pat. Nos. 9,435,687, 10,670,512, and U.S. application Ser. No. 16/888,660, incorporated herein in their entirety by reference. Alternatively, as will be explained below, the intrinsic spectrum in a library of known spectra can be generated by intrinsic spectral construction through the composite/addition of the intrinsic components, e.g., absorption, excitation, emission, as determined by classical spectrometry instrumentation. It is also envisioned that a combination of both methods can be used together to construct the library of known spectra, where some of the known spectra is determined directly via intrinsic spectrometry instrumentation and other known spectra is determined via the composite/addition of the intrinsic components, as will be explained below.

Figure 1B:
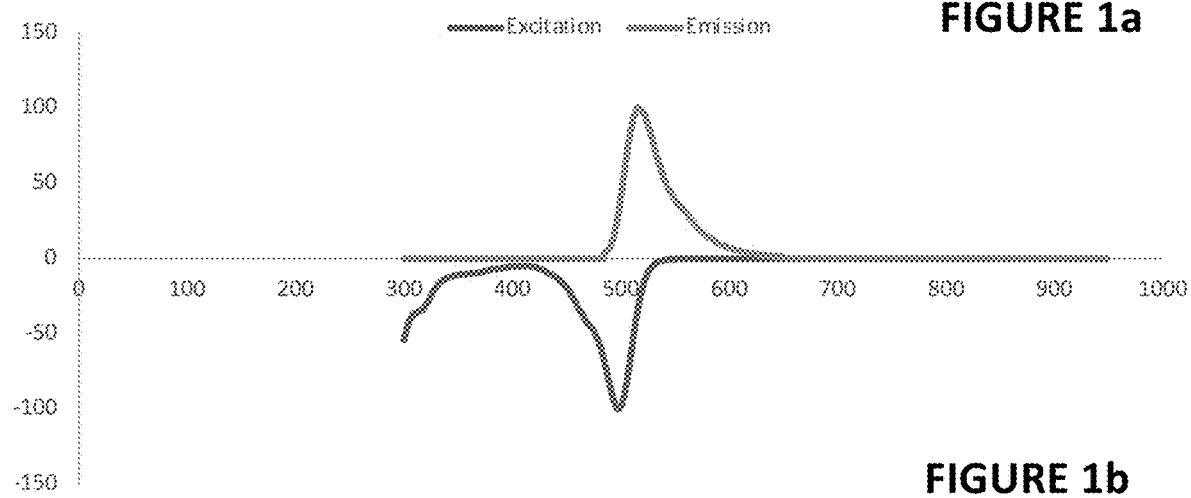
FIG. 1b shows the absorption components of FIG. 1a, generated by multiplying the intensities of the excitation component by minus one (−1) together with the emission component.

By definition, the unique fluorescent absorption and emission components of a dye are intrinsic since they do not contain any of the irrelevant spectral components of the illumination. The first step in creating an intrinsic fluorescence channel library requires the generation of the intrinsic spectrum of each fluorochrome from their absorption and emission components. The intrinsic spectrum of each fluorochrome is generated by adding the intensities of the respective absorption and emission components across the entire wavelength range of the illumination, as shown in FIG. 1. In turn, the intrinsic spectrum of each fluorochrome can be added together to form an Intrinsic Spectrum of the Totality for a sample assay. The Intrinsic Spectrum of Totality can be validated in two ways:

(1) mathematically, by stepwise subtracting the intrinsic spectrum of each fluorochrome from the Intrinsic Spectrum of Totality to yield a Zero Order Spectrum, i.e., a spectrum that has zero values across the illumination wavelength range.

(2) empirical by direct comparison of the actual intrinsic spectrum of a cell population labeled with all the fluorochromes in the assay.

Figure 2:
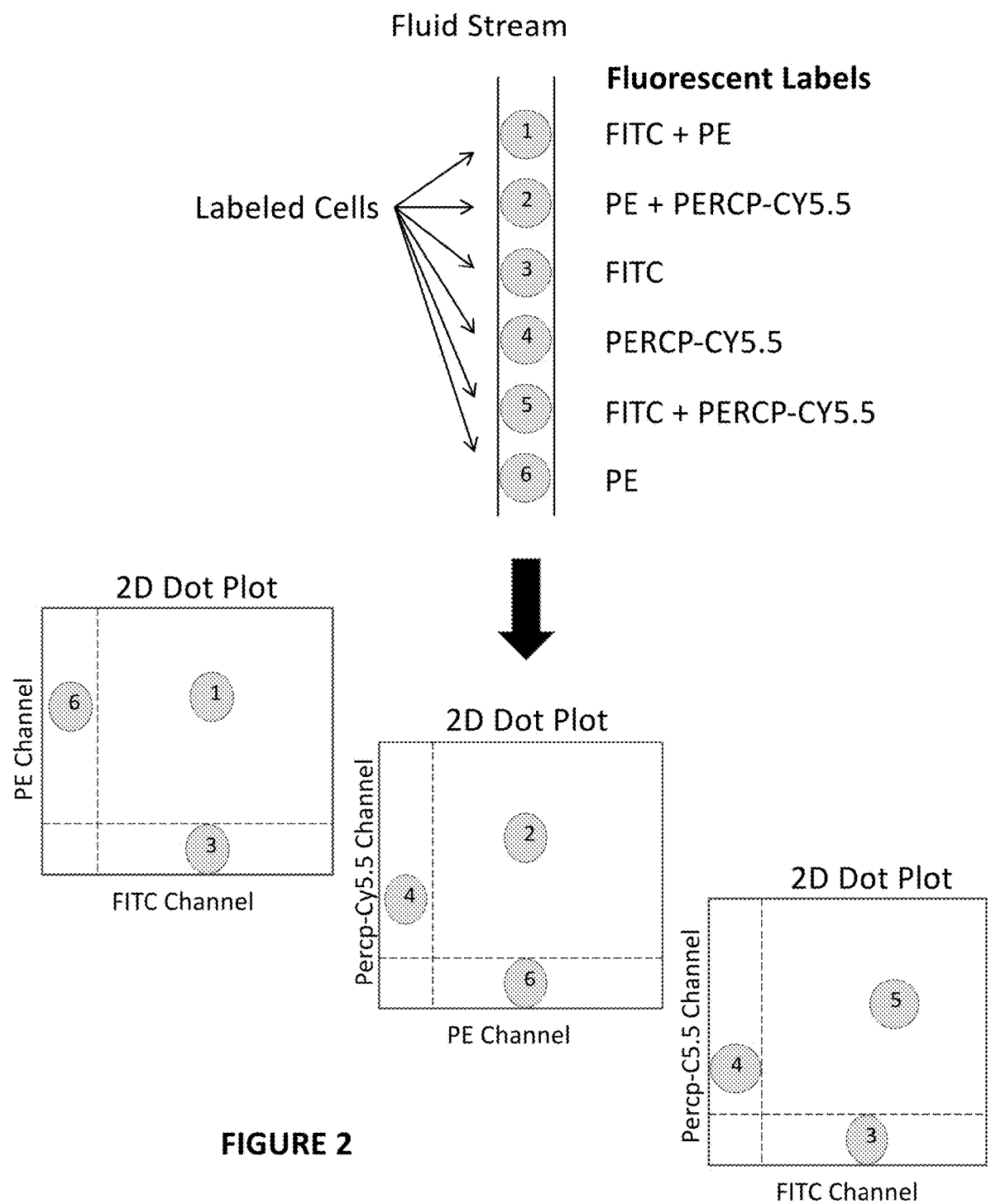
FIG. 2 shows an illustration of how cells labeled with different fluorochrome combinations are distributed into intrinsic 2D dot plots.

The fluorescence channels representing each intrinsic spectrum of the single and combined fluorochrome labels are equivalent to those normally defined by narrow band pass filters and represented as the axes of two-dimensional dot plots shown in FIG. 2. The single intrinsic spectrum axes of 2D dot plots can be obtained from multi-fluorochrome labeled samples by a two-step process where, first, all but two of the intrinsic spectra of the fluorochromes are subtracted from the complete Intrinsic Spectrum of Totality. The resulting sets of two intrinsic spectra represent channels labeled with pairs of the chosen fluorochromes. These intrinsic spectra can be further de-convoluted into the two individual intrinsic spectra by subtracting one of the intrinsic spectra from the combination of the two intrinsic spectra (IS) to serve as the axes of the dot plots. According to FIG. 2, this can be represented for FITC and PE by the following formulae:

$$IS(FITC)=[IS(FITC)+IS(PE)]-IS(PE) \quad (1)$$

$$IS(PE)=[IS(FITC)+IS(PE)]-IS(FITC) \quad (2)$$

The traditional dot plot format for immunophenotyping works only up to three fluorochromes. The number of 2D dot plots can become overwhelming and confusing especially attempting to represent multi-dimensional dot plots.

This situation may be represented mathematically by the equation that describes combinations:

$$\text{Number of combinations}=(n!/r!(n-r)!) \quad (2)$$

where: n is the number of fluorochromes, and r is the number of fluorochromes taken in combination per dot plot.

For example, if there are three fluorochromes used, the number of 2D dot plots required are:

$$\text{Number of 2D Dot Plots}=3!/2!(3-2)!=(3\times2\times1)/(2\times1)\times(1)=6/2=3$$

However, if there are ten fluorochromes are present, then the number of 2D dot plots required are:

$$\text{Number of 2D Dot Plots}=10!/2!(10-2)!=(10\times9)/(2\times1)=90/2=45$$

Application of Intrinsic Fluorescence Channel Library

As the demand increased for poly-chromatic immunophenotyping, automated software-implemented solutions to manage multi-dimensional color compensation were required. With the implementation of multi lasers and dozens of dyes, such immunophenotyping strategy was impractical. Ten fluorochromes generates forty-five 2D dot plots, a situation which is not trivial in terms of gating and re-gating to isolate specific sub-populations of cells. This traditional dot plot approach would require generating an additional larger number of difficult to visualize 3D and higher dimensionality dot plots that represent cell populations that bind combination of three or more different fluorescence labels.

However, the present invention solves these problems following returning principles of data management. The basic analytical data required for immunophenotyping:
(1) isolation of cell populations
(2) report the number of cells in each analyzed population
(3) report fluorescence intensity distribution of cell populations of interest The use of intrinsic spectra according to the present invention to define fluorescence channels provides a simple solution to obtaining these data.

For example, consider a library of fluorescence channels for ten fluorochromes that for practical purposes, is limited to cells that bind four or less different fluorochrome labeled antibodies that would generate the following channels plus one channel for unlabeled cell populations:

TABLE 1

Number of Intrinsic Fluorescence Channels

| | |
|---|---|
| 10!/1!(10-1)! | 10 |
| 10!/2!(10-2)! | 45 |
| 10!/3!(10-3)! | 120 |
| 10!/4!(10-4)! | 210 |
| Unlabeled | 1 |
| Total | 386 |

To employ the de-convolution methodology of fluorescing cells according to the invention, a complete library of known intrinsic fluorescence channels is pre-determined and are stored in the instrument's computer. Alternatively, the complete library of known intrinsic fluorescence channels is stored remotely from the instrument.

In accordance to a preferred embodiment in flow cytometry, as the cells pass through the interrogation point, the intrinsic spectrum of each cell is compared to the whole intrinsic spectrum, with respect to the wavelength positions of maxima, minima and profile, i.e., shape, of the intrinsic spectra in the library of known intrinsic spectra that is defining a particular fluorescence channel. Each labelled cell is assigned to its matching fluorescence channel. The number of cells that fall within each of the single and multiple intrinsic fluorochrome channels is directly determined without the use of error prone subjective gates. Antibody binding capacity (ABC) of each cell population can be represented by an intensity histogram of each intrinsic fluorescence channel, respectively.

This methodology provides precisely defined fluorescence channels for the intrinsic flow cytometer libraries because the individual contributions of intrinsic components of the spectra are determined by the excitation and emission components determined by spectrofluorometers. The intrinsic components of each fluorochrome can be combined into its respective spectrum. By combining the intrinsic spectra of the fluorochromes in an assay, all the intrinsic spectra added, generates the intrinsic spectrum of totality for the assay. By de-convoluting the intrinsic spectrum of totality, a library of known intrinsic spectra can be produced that represent all of fluorescence channels representing the individual fluorochromes, as well as, any combination of fluorochrome labeled cell populations, thereof.

Although in accordance to a preferred embodiment, these methodologies were developed for intrinsic flow cytometers, they are not limited to this instrumentation. It should be noted that intrinsic flow cytometry presents the most well-defined application considering the small number of fluorochromes used in any assay, and whose intrinsic spectra can easily be generated since all of their intrinsic components, excitation (absorption) and emission are easily determined with a spectrofluorometer.

In the case of Intrinsic Imaging instruments, i.e., cameras, that produce intrinsic spectra associated with each pixel of a field of view, many of the contributing intrinsic spectra may be unknown, so identification of all the materials in an image may not be feasible. However, the de-convolute methodology of the present invention provides a powerful tool to positively determine the presence or absence of the specific materials of intrinsic spectra. The intrinsic spectra of the library can be compared to the intrinsic spectrum associated with each pixel of an multi-spectral or hyper-spectral image to determine the spatial location and associations of these known materials in the image. These locations can, for example, be presented in an isolation display by assigning an intensity value of zero to all pixels in the image that do not have a match with intrinsic spectra in the Library. The resulting image of matching pixels appear as they do in the original image, but on a black background. Alternatively, the intensity value of the matching pixels can be increased by an appropriate factor, e.g., a factor of 2 to 10 times, to have the known material or materials clearly stand out in the image.

It is to be understood, that according to another embodiment of the present invention, the library of known intrinsic spectra can also comprise of a single intrinsic spectral channel assigned to the intrinsic spectra of at least one known material of interest.

EXAMPLES

In these examples, excitation and emission spectra wavelength range covered UV to near IR (300-949 nm). The data was obtained from a ThermoFisher SpectraViewer (thermofisher.com). The excitation spectra were converted to absorption spectra by multiplying the excitation intensities by minus one (−1). Both the absorption and emission spectra met the criteria of being intrinsic spectral components since they were devoid of irrelevant illumination spectral components.

Example 1: De-Convolution Methodology of Intrinsic Spectral Components

Figure 1C:
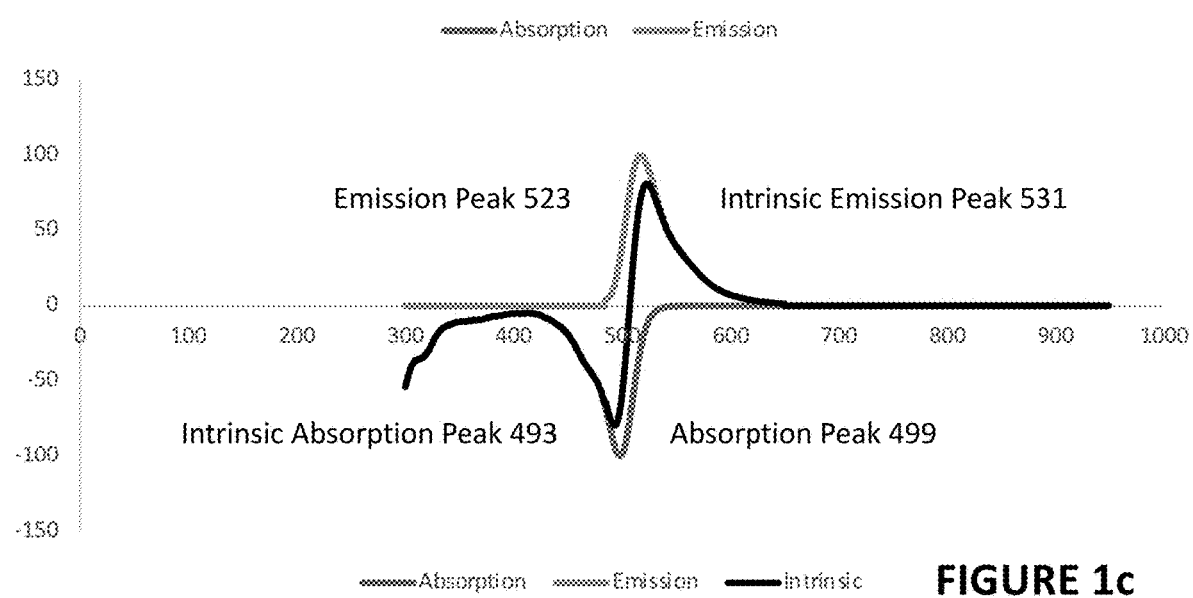
FIG. 1c shows the intrinsic spectrum of FITC generated by adding the emission and absorption spectra shown in FIG. 1b.

Since an intrinsic fluorescence spectrum contains only spectral components that are generated from absorption of illumination energy, it follows that an intrinsic spectrum is the sum of intrinsic spectral components, specifically, absorption and emission. Therefore, adding the absorption and emission spectral components of a fluorochrome will produce the intrinsic fluorescence spectrum of the fluorochrome, as illustrated with fluorescein in FIG. 1b. Note that the peak positions of both the absorption and emission profiles in the intrinsic spectrum are slightly decreased and shifted from those components when isolated. These spectral shifts occur when the absorption (negative values) and the emission (positive values) of the spectra are added together in the wavelength region of overlap, as shown in FIG. 1c. Subtracting either the absorption or emission components from the intrinsic spectrum to obtain the original emission or absorption components, respectively, can validate this.

Example 2: De-Convolution Methodology of Intrinsic Spectra

Figure 3A:
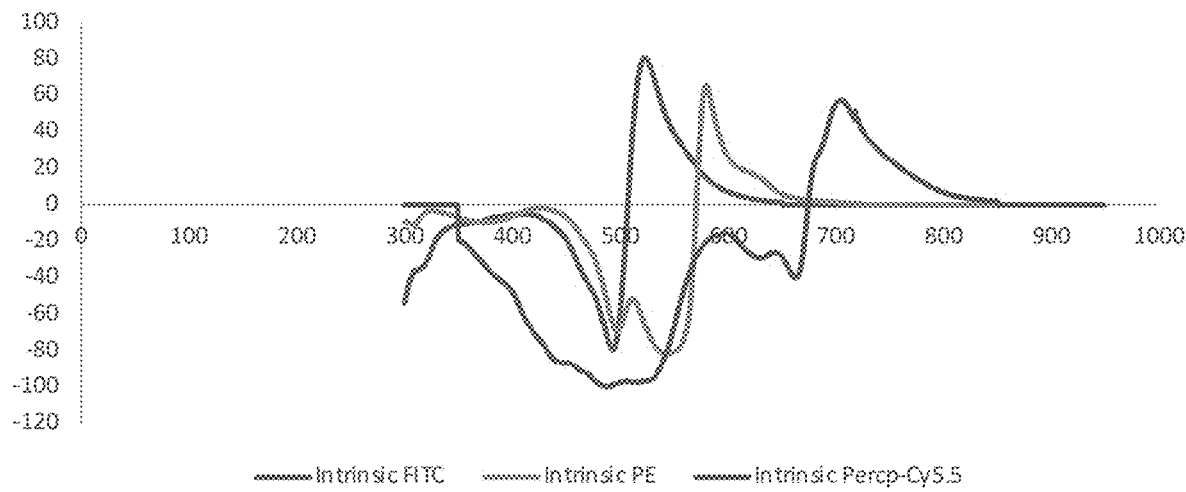
FIG. 3a shows the three superimposed intrinsic spectra of: FITC, PE, and Percp-Cy5.5, according to an embodiment of the invention.
Figure 3B:
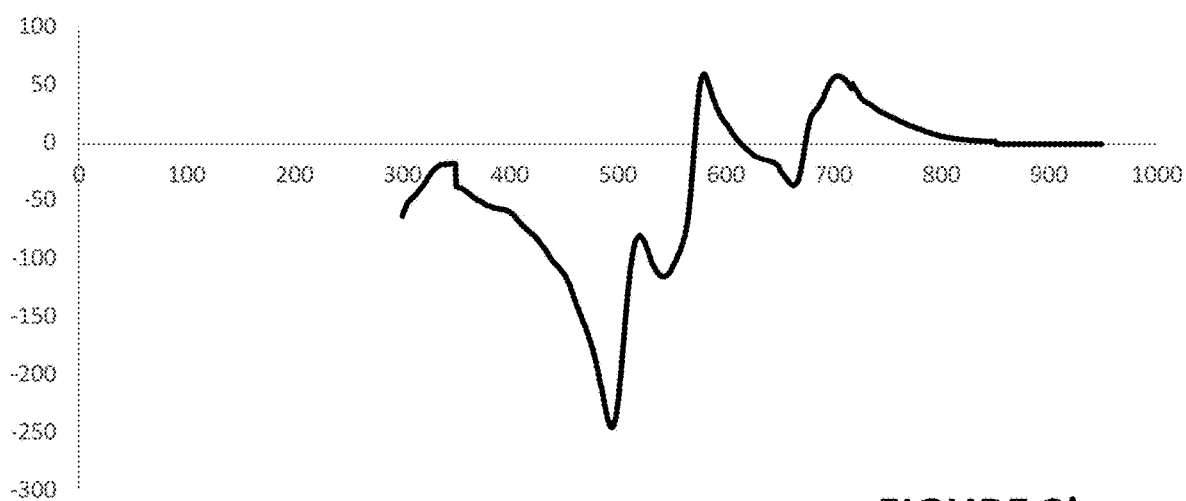
FIG. 3b shows the total Intrinsic Spectrum generated by adding the intensities of all three intrinsic fluorochrome spectra.

Similar to Example 1, intrinsic spectra can be added together to form composite intrinsic spectra. For example, the Intrinsic Spectra of Totality comprised of FITC, PE and Percp-Cy5.5 can be formed by adding the intrinsic spectrum of each fluorochrome together, as illustrated in FIG. 3a. Such individual and combined intrinsic spectra are the basic elements of the reference library of fluorescence channels for a specific assay. This combination of three fluorochromes, represent the Intrinsic Spectrum of Totality, as shown in FIG. 3b.

Example 3: Construction of a Simple Intrinsic Fluorescence Channels Library

Figure 4:
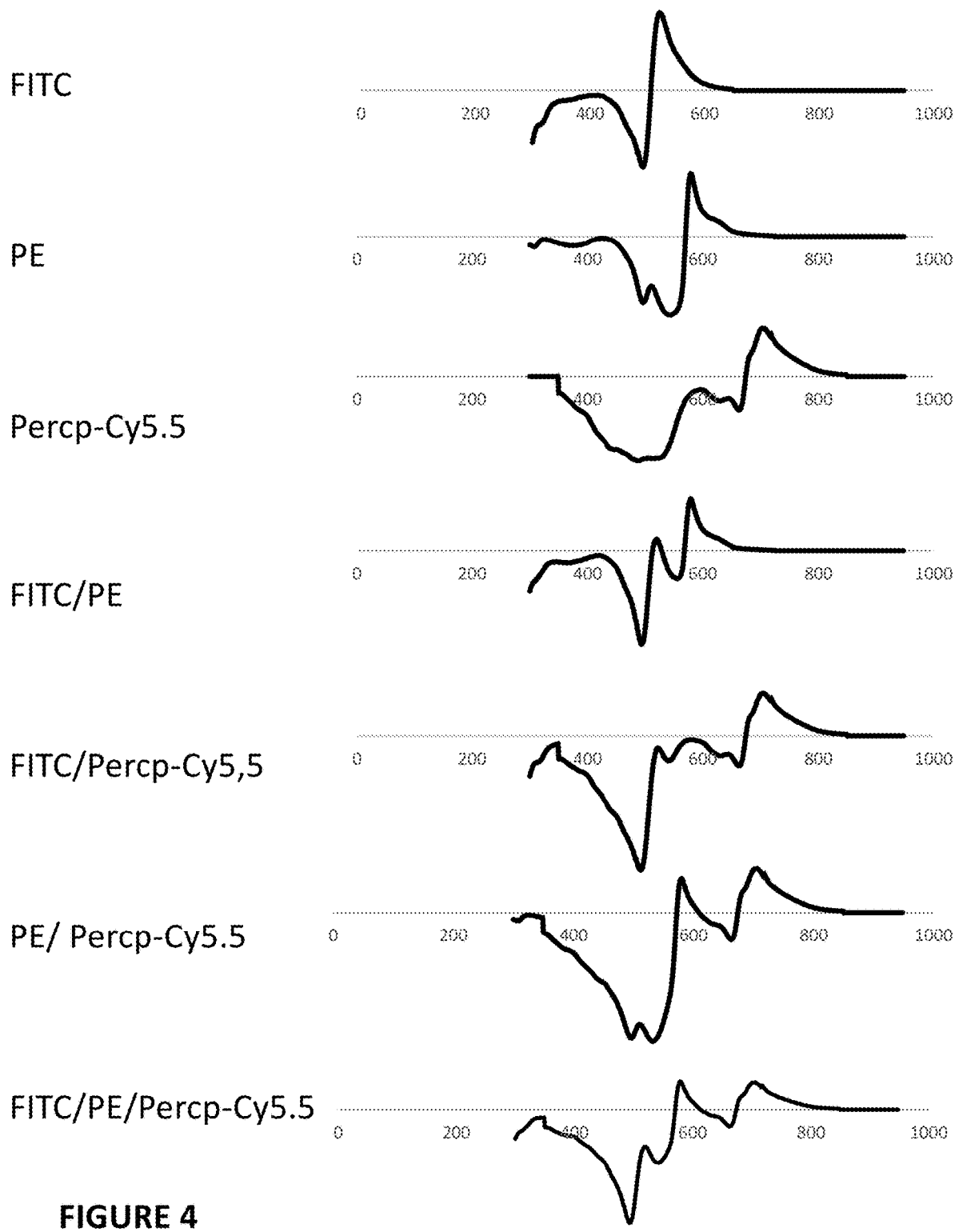
FIG. 4 illustrates the library of known intrinsic spectra defining fluorescence channels for single and combinates of intrinsic spectra of FITC, PE, and Percp-Cy5.5.

A library of fluorescence reference channels was created for FITC, PE and Percp-Cy5.5. These three intrinsic spectra, as generated in Example 1, are then added together to form an Intrinsic Spectrum of Totality. This intrinsic spectrum of totality was then de-convoluted to create the three double-labeled fluorescence channels that represent the other combinations of possible fluorescence binding to cells in this assay, as illustrated in FIG. 4. The de-convolution was accomplished by subtracting the intrinsic spectrum of each fluorochrome from the intrinsic spectrum of totality in turn to produce three intrinsic spectra representing double labeled cells, i.e., FITC/PE, FITC/Percp-Cy5.5 and PE/Percp-Cy5.5. The Intrinsic Spectrum of Totality contains all three fluorochromes and represents the seventh fluorescence channel. An eighth channel is required in the library to represent cells that were unlabeled.

Figure 5:
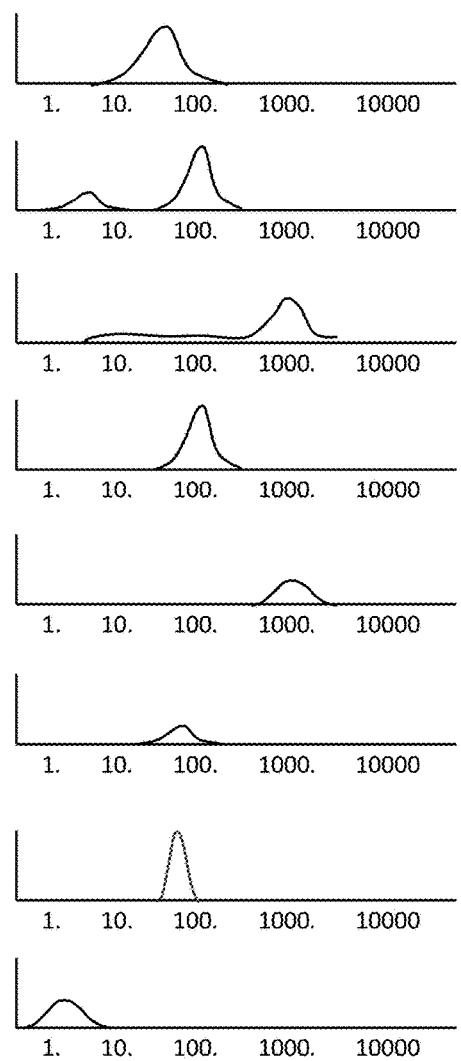
FIG. 5 shows a simulated Intrinsic Flow Cytometer Analysis Report of a blood sample labeled with FITC-CD3, PE-CD4, and Percp-Cy5.5-CD8, where the total number of cells analyzed, the percent of cells in each intrinsic fluorescence channel and the log plots of intensity of the cells in each channel are presented.

Example 4: Simulation of an Intrinsic Spectral Analysis Report of a Multi Fluorochrome Labeled Blood Health human blood is stained with FITC-CD3 and PE-CD4 and Percp-Cy5.5-CD8 antibodies. The intrinsic flow cytometer detects the intrinsic spectrum of each cell that passes through the fluorescence detection system. The intrinsic spectrum of each cell is matched with one of the intrinsic fluorescence channels in the Library of Known Intrinsic Fluorescence Channels previously generated in Example 3. Each matched cell, along with its intensity, is assigned to its respective fluorescence channel. The analysis reports the number of cells in each channel and a plotted of their intensity as a simple histogram, as illustrated in FIG. 5. Note that the T-lymphocytes are cells that bind to both CD3 and CD4 and are isolated in the FITC/PE fluorescence channel while the CD8 T-lymphocytes are isolated in the PE channel.

Example 5: Simulation of the De-Convolution Methodology Applied to Imaging

Figure 6:
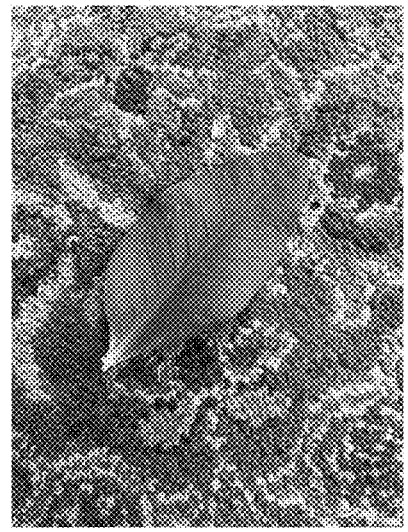
FIG. 6 shows images of a focused image of a field of view (a), an unfocused image of the same field of view (b), and the intrinsic image of the same field of view (c), according to an embodiment of the present invention.
Figure 6:
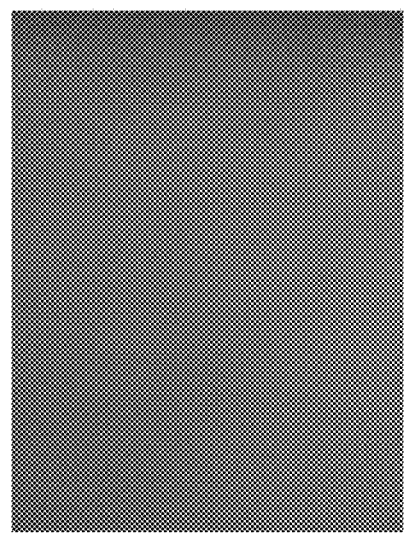
Figure 6:
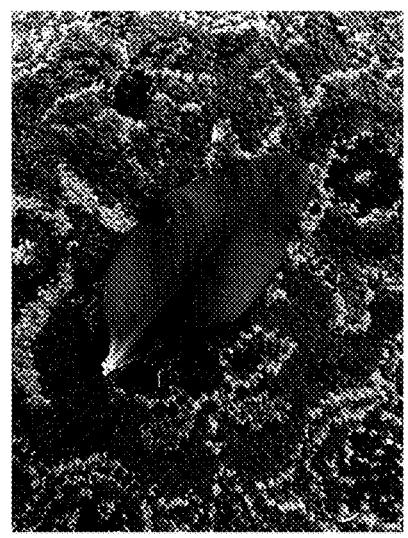
Figure 7A:
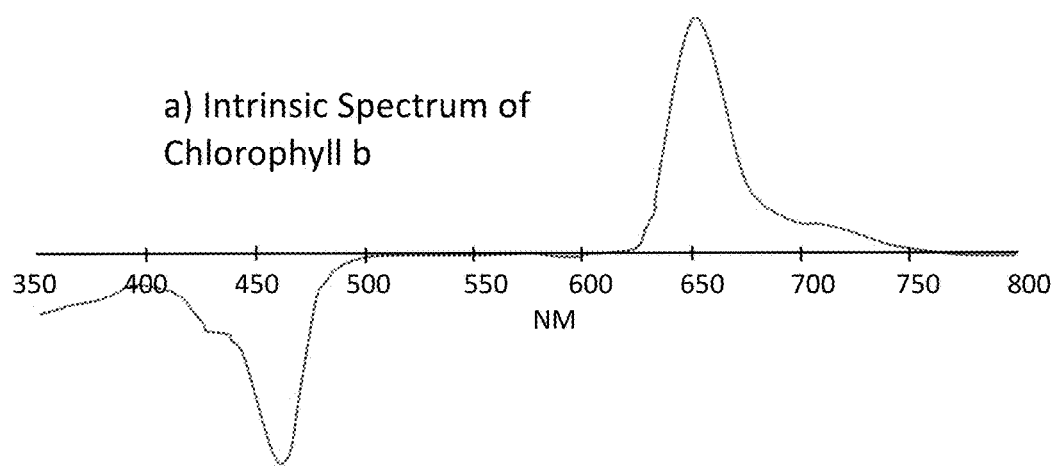
FIG. 7a shows a simulated intrinsic spectrum of chlorophyll b.
Figure 7B:
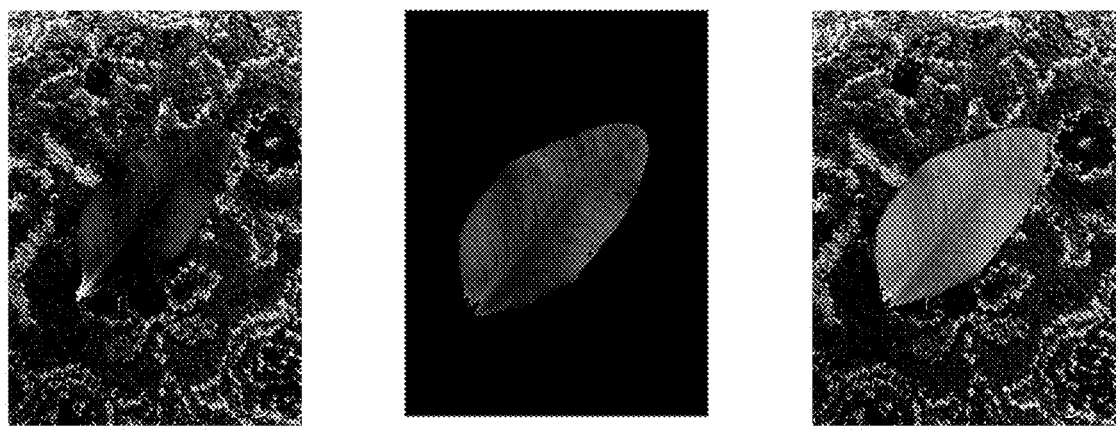
FIG. 7b shows images of the regions of isolated chlorophyll b, and of the regions of enhanced chlorophyll b, according to an embodiment of the present invention.

An intrinsic hyper-spectral image is obtained of a field of view that is suspected of containing several specific known materials. The intrinsic image is generated by removing the irrelevant illumination as described in U.S. Pat. No. 10,652,484 or U.S. application Ser. No. 16/888,660, incorporated herein in their entirety by reference. This is accomplished by taking a focused image of the field of view, as seen in FIG. 6a, followed by an unfocused or translucent image of the same field of view such that no spatial detail is present in the second image, shown in FIG. 6b. This set of images are processed by the intrinsic methodology described in the above-referenced patent documents. The intrinsic spectra of these known materials are obtained from samples of the isolated known materials or from know intrinsic spectral components of the respective known materials. A Library of Intrinsic Spectra of Materials is generated from the intrinsic spectra of the materials suspected to be present in the image, including the individual intrinsic spectra and all combination, thereof. By choosing an intrinsic spectrum from the Library of the suspected materials of being present in the field of view, e.g. chlorophyll b, shown in FIG. 7a, the intrinsic spectrum of each pixel of the image is compared to the intrinsic spectrum of chlorophyll in the Library. The regions of matching intrinsic spectra in the image can then be displayed as the isolated areas of chlorophyll b or displayed as enhanced regions (e.g., brightness, contrast, saturation, hue, etc. . . . ) of the field of view, as shown in FIG. 7b.

Although the present invention has been described herein with reference to the foregoing exemplary embodiment, this embodiment does not serve to limit the scope of the present invention. Accordingly, those skilled in the art to which the present invention pertains will appreciate that various modifications are possible, without departing from the technical spirit of the present invention.

The invention claimed is:

1. A method of creating a library of known intrinsic spectra of known materials, said method comprising:
    obtaining intrinsic spectra of each known material of a plurality of known materials;
    generating a known intrinsic spectrum of totality by adding together the intrinsic spectra of each known material;
    individually subtracting the intrinsic spectra of said each know material, and all combinations thereof, from the intrinsic spectrum of totality to obtain a plurality of individual composite known intrinsic spectra resulting from said individual subtractions; and
    assigning the intrinsic spectra of each known material, the known intrinsic spectrum of totality and the plurality of individual composite known intrinsic spectra to define individual intrinsic spectra channels of said library of known intrinsic spectra, wherein the assigned intrinsic spectra of each intrinsic spectra channel is correlated to at least one known material of said plurality of known materials.

2. The method according to claim 1, wherein the intrinsic spectra of each known material is determined by adding at respective wavelengths the intensities of intrinsic absorption spectra and intrinsic emission spectra of said known material.

3. The method according to claim 2, wherein said intrinsic absorption spectra is obtained by multiplying by minus one (−1) the intensities of intrinsic excitation spectra of said known material.

4. The method according to claim 1, wherein said library of known intrinsic spectra further includes an intrinsic spectral channel corresponding to unknown intrinsic spectra.

5. The method according to claim 1, wherein said at least one known material comprises a fluorescent labeling material.

6. The method according to claim 5, wherein said individual intrinsic spectral channels represents fluorescence channels defined by a shape of known intrinsic spectra of said at least one known fluorescent labeling material.

7. The method according to claim 1, wherein the intrinsic spectra of at least one known material is determined directly from the at least one known material by means of intrinsic spectrometry instrumentation.

* * * * *